United States Patent [19]
Morales

[11] Patent Number: 5,893,852
[45] Date of Patent: Apr. 13, 1999

[54] STENT CRIMPING TOOL AND METHOD OF USE

[75] Inventor: Stephen A. Morales, Mountain View, Calif.

[73] Assignee: Advanced Cardiovascular Systems, Inc., Santa Clara, Calif.

[21] Appl. No.: 09/069,011

[22] Filed: Apr. 28, 1998

[51] Int. Cl.⁶ .................................................. A61M 29/00
[52] U.S. Cl. ........................................................ 606/108
[58] Field of Search ........................... 606/198, 191–195, 606/1, 108; 29/515, 516

[56] References Cited

U.S. PATENT DOCUMENTS

| | | |
|---|---|---|
| 696,289 | 3/1902 | Williams . |
| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,189,786 | 3/1993 | Ishikawa et al. . |
| 5,437,083 | 8/1995 | Williams et al. . |
| 5,546,646 | 8/1996 | Williams et al. . |
| 5,626,604 | 5/1997 | Cottone, Jr. ...................... 606/108 X |
| 5,630,830 | 5/1997 | Verbeek . |
| 5,653,691 | 8/1997 | Rupp et al. . |
| 5,738,674 | 4/1998 | Williams et al. . |
| 5,746,764 | 5/1998 | Green et al. . |
| 5,783,227 | 7/1998 | Dunham . |
| 5,785,715 | 7/1998 | Schatz . |

FOREIGN PATENT DOCUMENTS

| | | |
|---|---|---|
| 159065 | 2/1921 | United Kingdom . |
| WO 98/14120 | 4/1998 | WIPO . |
| WO 98/19633 | 5/1998 | WIPO . |

OTHER PUBLICATIONS

U.S. Patent Application Serial No. 08/795,335 filed Feb. 4, 1997.
U.S. Patent Application Serial No. 08/837,771 filed Apr. 22, 1997.
U.S. Patent Application Serial No. 08/089,936 filed Jul. 15, 1997.
U.S. Patent Application Serial No. 08/962,632 filed Nov. 3, 1997.
*The eXTraordinary Stent,* C.R. Bard Brochure (Undated).

*Primary Examiner*—Michael Buiz
*Assistant Examiner*—Vikki Trinh
*Attorney, Agent, or Firm*—Fulwider Patton Lee & Utecht, LLP

[57] ABSTRACT

A stent crimping tool for firmly and uniformly crimping a conventional or radioactive stent onto a balloon catheter is constructed from a proximal section rotatably connected to a distal section, the two cylindrical sections forming the transparent housing. A cylindrical cavity having a tapered end is formed into the proximal section. Inside the cavity is affixed a transparent cylindrical collar having radial slots leading to a central passage extending along its axis, and a conical end that fits into the tapered end. Teeth made of trapezoidal shape flat plates each having an angular proximal edge and a radiused edge slide into their respective slots in the collar. A transparent screw feed having a hollow core and a slotted head that receives the radiused edge of each tooth/plate is threaded to the distal section. A balloon catheter is passed through a passage in the proximal section and the collar and an uncrimped stent positioned in the hollow core of the screw is loaded thereon. Rotating the distal section of the housing advances the screw and plates toward the tapered cavity, which has angled walls that force the plates to converge radially inward. This convergence causes the radiused edges of the plates to collectively crimp the stent onto the balloon.

22 Claims, 6 Drawing Sheets

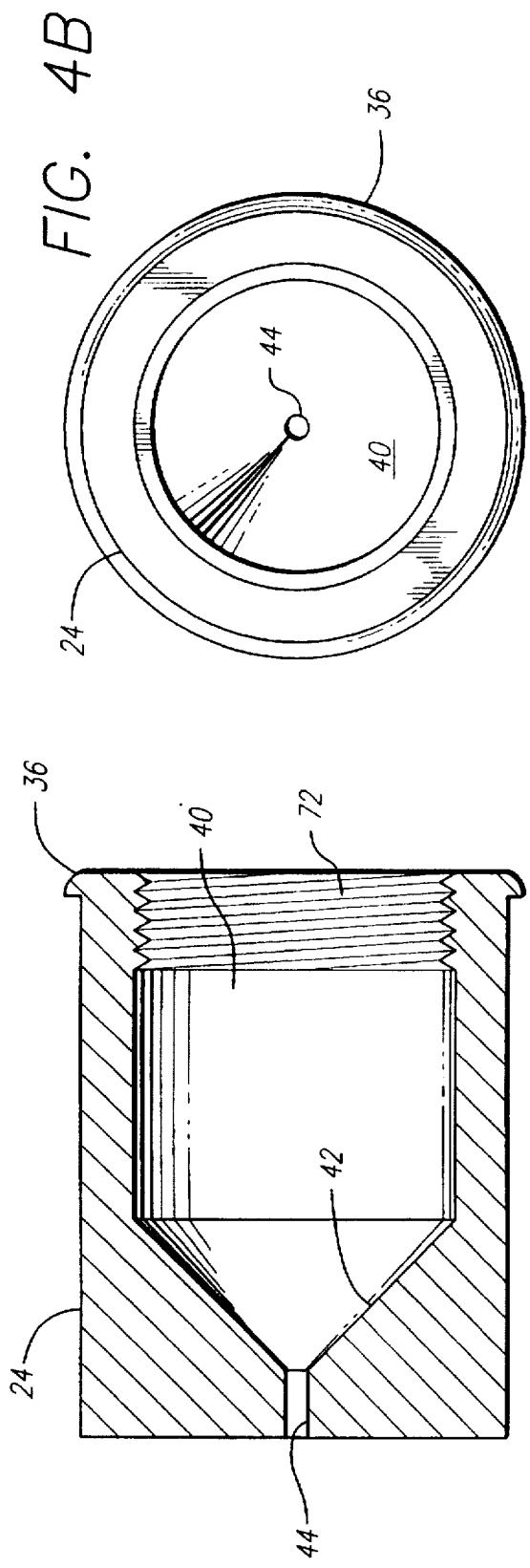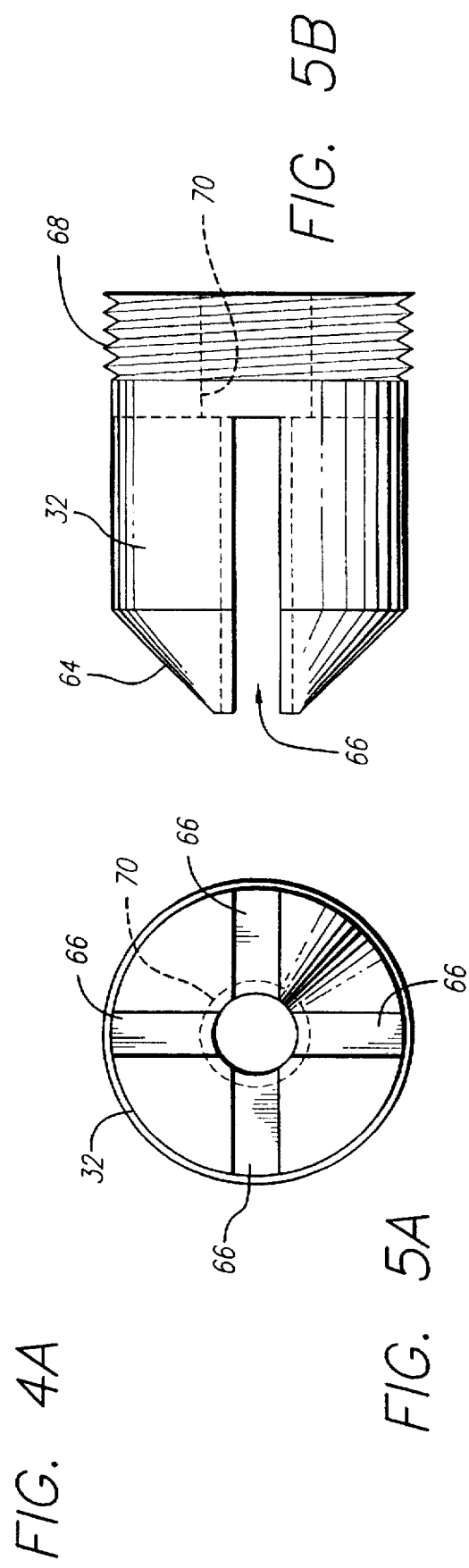

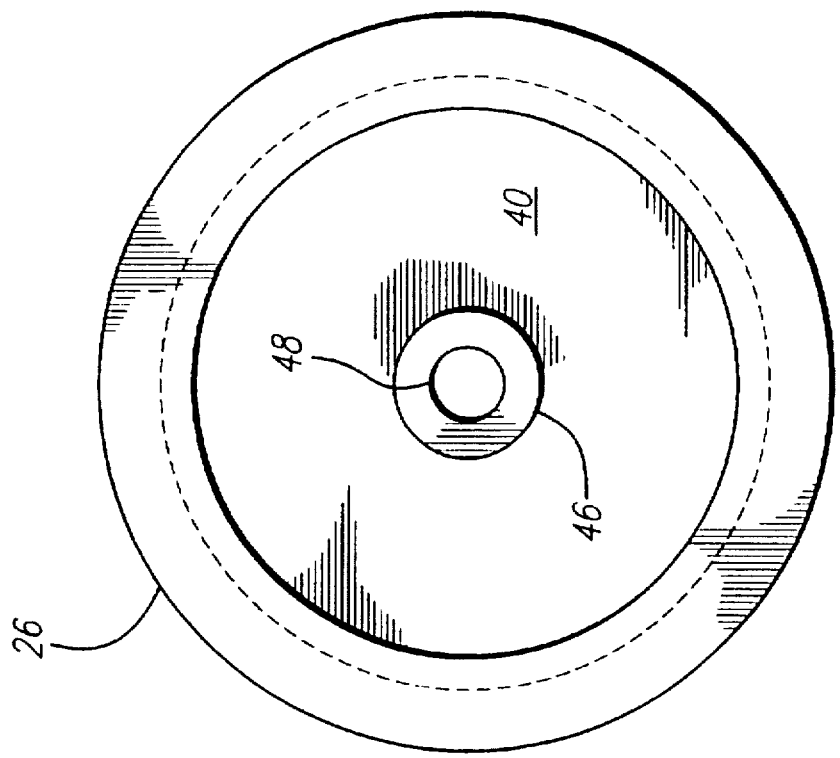
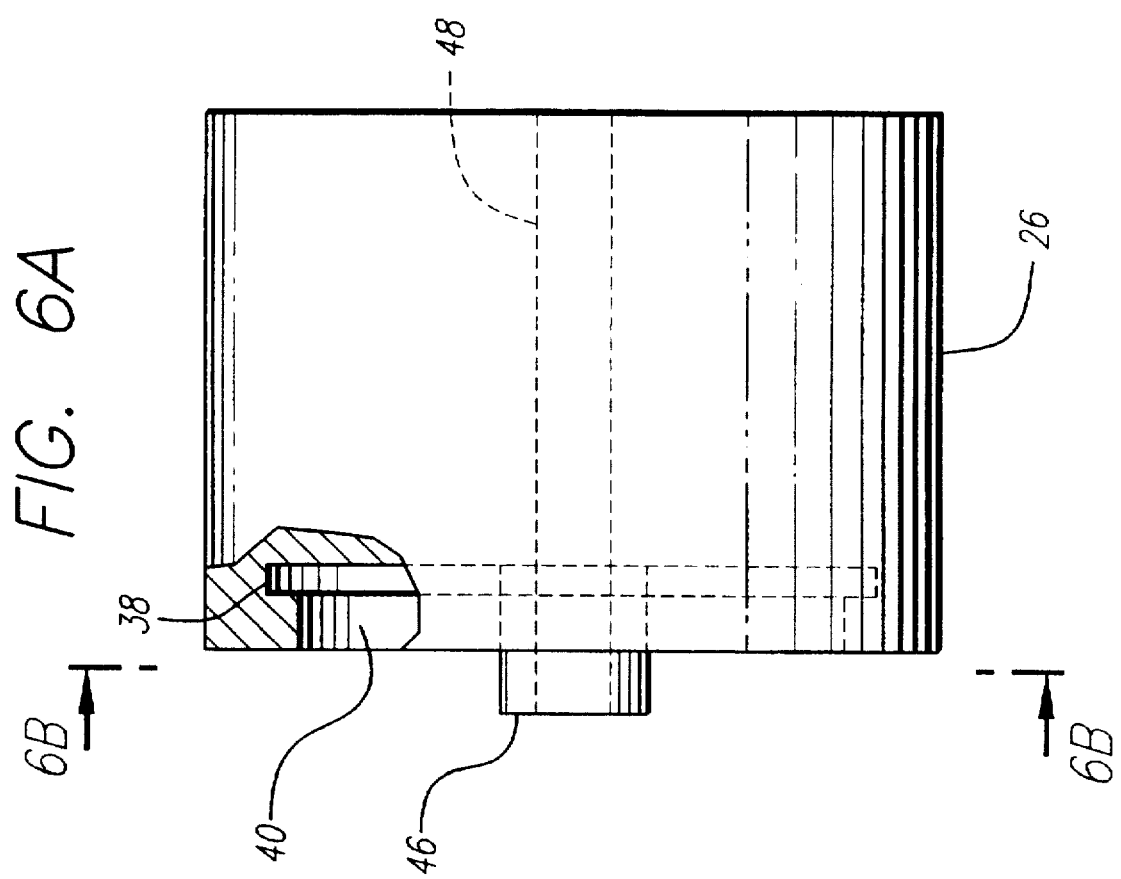

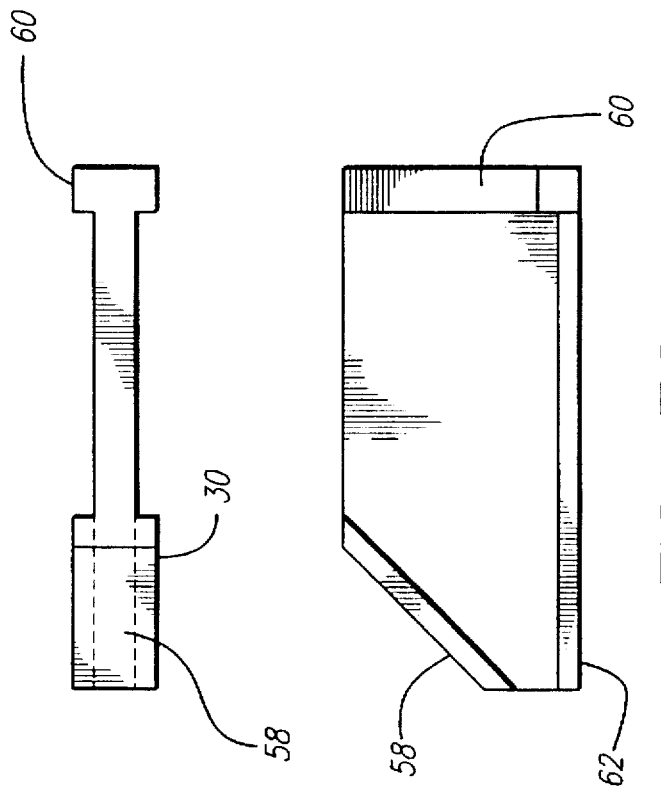
FIG. 7A
FIG. 7C
FIG. 7B
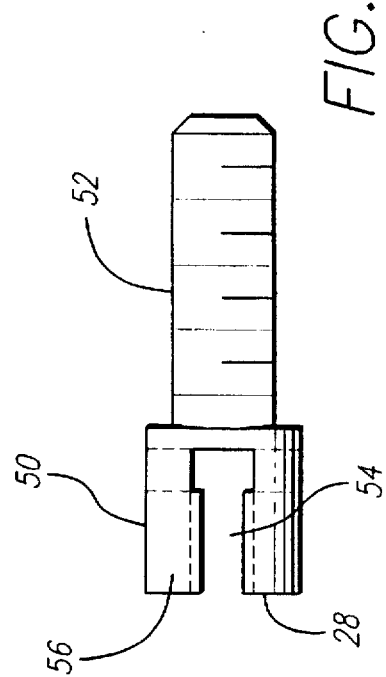
FIG. 8B
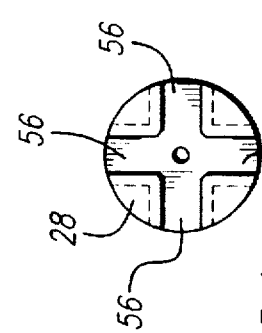
FIG. 8A

STENT CRIMPING TOOL AND METHOD OF USE

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, nonuniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform or loosely applied crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which would be antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed from a rigid, tubular body with a ball at one end connected to a plurality of long, thin strips passing through the tubular body. An uncrimped stent is placed over the plurality of long, thin strips, which hold the stent in an expanded state. The balloon portion of a catheter is inserted into the cylindrical space formed by the plurality of strips. When the user pulls the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps. Consequently, they are unsuitable for use by physicians in a cath lab who desire to crimp the stent onto the balloon catheter.

SUMMARY OF THE INVENTION

Both PTCA and PTA procedures have become commonplace in treating stenoses or lesions in blood vessels and coronary arteries. In approximately 35% to 40% of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to ensure that the stent stays on the balloon until the balloon is expanded and the stent is implanted in the vessel. The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon.

In a preferred embodiment, the present invention is directed to a tool for crimping a stent onto a balloon catheter, comprising a housing including a proximal section and a distal section, wherein the proximal section includes a cylindrical cavity having a tapered end, and an opening in communication with the cavity; a cylindrical collar having a conical end conforming to the tapered end when the collar is positioned therein, wherein the collar further includes a plurality of slots extending radially and along a length thereof and intersecting at the conical end, and having a passage therethrough that is in communication with the opening in the proximal section; a plurality of teeth having a plate shape, each tooth/plate having an angular proximal edge, and being slidably disposed inside a corresponding slot in the collar, each plate having a radiused edge extending into the passage; and a screw feed extending into the passage wherein the screw feed includes radial slots that lead into a hollow core, and wherein the slots receive the respective radiused edges of the plates extending therein, and wherein the screw feed is threaded to the distal section of the housing.

An uncrimped stent is manually loaded into the hollow core. At the opposite end of the tool, the balloon catheter is inserted through the opening into the cylindrical cavity at the proximal section of the housing, which leads into the hollow core of the screw holding the uncrimped stent.

Ideally, the invention is held in the user's dominant had while the other hand advances a balloon catheter into the hollow core holding the stent. In the preferred embodiment, the present invention crimping tool is made from a transparent or translucent material so that the user can watch the insertion of the balloon catheter. Looking into the hollow core of the screw feed, the user manually aligns and loads the uncrimped stent on to the balloon catheter.

Alternatively, the present invention tool can be advanced over a guide wire. Next, the balloon catheter is advanced along the guide wire and fed into the hollow core holding the uncrimped stent. The stent is then loaded onto the balloon portion of the catheter.

In the exemplary embodiment, a mandrel or a wire is inserted into the tool with the balloon catheter. The mandrel helps the balloon catheter maintain its shape during the crimping process. Otherwise, the crimp on the stent may be imperfect and there may be damage to the balloon catheter when the stent is crimped too far. In an alternative embodiment, a mandrel may be built into the tool so that it extends therefrom, and the catheter is guided onto the mandrel and into the correct position every time.

With the stent loaded onto the balloon portion of the catheter, a surgeon or a technician in a cath lab can manually yet precisely crimp the stent using the present invention tool. Holding the tool in his or her hands, the surgeon twists the distal section of the housing to perform the crimp.

The rotational motion of the distal section of the housing is translated into linear displacement of the screw feed by the following process. First, the distal section and the proximal section are clipped together to permit relative rotation but to prevent relative linear displacement. Second, the collar is affixed to the proximal section so it cannot rotate, and the threaded screw feed likewise cannot rotate due to its linkage with the collar through the teeth/plates. Third, the rotation of the distal section causes the screw feed to rotate out of the distal section and to simultaneously advance linearly toward the proximal end of the tool.

As this occurs, the angular proximal edge of each tooth/plate is carried by the advancing screw feed into engagement with the tapered end, resulting in contact and sliding displacement of the teeth/plates radially inward toward a central axis of the tool. In unison, the radiused edges of the teeth/plates converge on the underlying stent to crimp the stent onto the balloon catheter. The radiused edges of the plates thus act as crimping jaws.

The present invention also features an optional visual indicator to assist the user in crimping the stent. Specifically, once the balloon catheter and the stent are aligned, the distal section is twisted or screwed until a marking on the exterior of the distal section reaches a red line painted on the exterior of the proximal section. The red line provides a visual cue to the user to stop twisting because the crimping step has been completed. Twisting the distal section beyond the red line creates a greater likelihood of damage to the balloon catheter due to excessive crimping.

After the crimping step is performed, the user unscrews the distal section of the housing so that the balloon catheter and the crimped stent can freely slide through the passage in the tool. If the balloon catheter and crimped stent do not easily slip through the crimping tool, then the foregoing crimping procedure needs to be repeated. To be sure, the process is repeated until the crimped stent safely passes through the crimping tool and into the patient.

The present invention represents an important step toward the handling of fragile stents. It also represents a significant reduction of the user's exposure to radioactive stents, because the walls of the present invention crimping tool are preferably thicker than ¼ inch so that they provide adequate shielding from the radioactive stent.

In addition, the radioactive stent can be packaged, shipped, and stored inside the present invention crimping tool for the length of its half life. When the stent is to be implanted, the user simply loads the stent—which is already inside the tool—onto the balloon catheter, twists and untwists the housing to crimp and release the stent, and feeds the crimped stent along the guide wire into the patient's vasculature. Thus, some benefits of the present invention tool are that it provides safe storage for the stent prior to implantation, while conveniently transforming into a crimping tool that does not require direct handling of the fragile stent.

The present invention tool is highly versatile. First, it is ideal for handling stents because the tool has a larger diameter than the stent, but is still centered on the stent's axis. Accordingly, the present invention tool allows physicians to correctly crimp a stent onto a balloon.

Second, it effectively establishes a reliable stent crimp on a balloon of any diameter. The reason is that the tool has an opening approximately twice the diameter of the stent to accommodate the stent and the balloon catheter.

Third, the radiused edge of each tooth/plate can be designed to press the stent and the balloon catheter down to a specified diameter. This dimension, of course, can be altered by changing the radius of the edges machined into the plates. Fourth, the present invention tool is intended to be used on a variety of stent lengths. The total length of a preferred embodiment tooth/plate is over thirty-five millimeters long, thereby accommodating the lengths of the stents currently on the market.

The present invention crimping tool can be used with any stent system which is released without a delivery system. Although the present invention tool is intended to be a disposable device, the tool may eventually be sold alone because its design is robust enough to undergo many repeated uses.

In summary, the present invention tool protects doctors from the dangers of beta radiation emitted from radioactive stents. Also, the present invention tool is capable of homogeneously and precisely crimping a stent onto a balloon catheter. Such a crimping tool is highly useful to cardiologists, for example. Such physicians are constantly concerned with proper deployment of the stent within the patient that it is desirable to have a consistently and reliably crimped stent. The present invention tool is further a time saver, because the stent crimping procedure can be performed fairly efficiently and quickly. These and other advantages of the present invention will become apparent from the following detailed description thereof when taken in conjunction with the accompanying exemplary drawings.

BRIEF DESCRIPTION OF THE DRAWINGS

FIGS. 4A and 4B are cross-sectional and rear elevational views, respectively, of a preferred embodiment proximal section of the housing.

FIGS. 5A and 5B are front elevational and side elevational views, respectively, of a preferred embodiment collar showing the orthogonal slots formed therein.

FIGS. 6A and 6B are side-elevational and front elevational views, respectively, of a preferred embodiment distal section of the housing.

FIGS. 7A, 7B, and 7C are top plan, front elevational, and side elevational views, respectively, of a preferred embodiment tooth having an angular proximal edge.

FIGS. 8A and 8B provide front elevational and side elevational views, respectively, of a preferred embodiment screw feed.

DETAILED DESCRIPTION OF THE PREFERRED EMBODIMENTS

Figure 1:
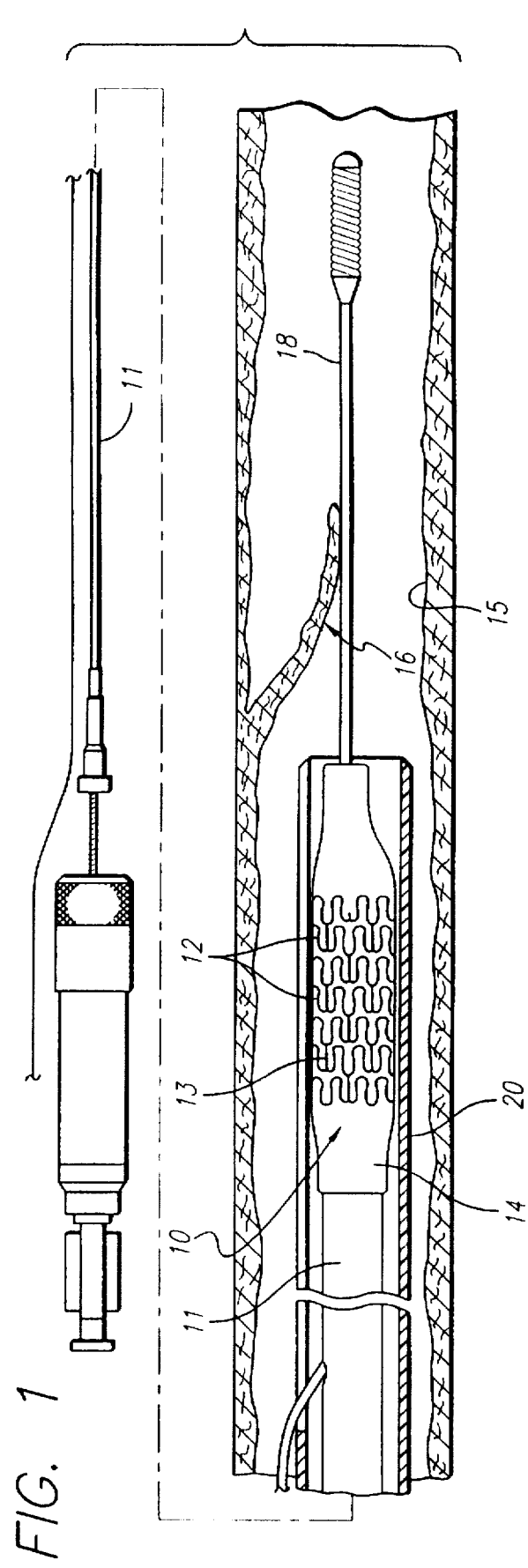
FIG. 1 is a side elevational view, partially in section, depicting a stent that has been crimped onto a delivery catheter and disposed within a vessel.

FIG. 1 illustrates intravascular stent 10 which is mounted onto delivery catheter 11. Stent 10 generally comprises a plurality of radially expandable cylindrical elements 12 disposed coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has dissected lining 16 which has occluded a portion of the arterial passageway.

Delivery catheter 11 onto which stent 10 is mounted is essentially the same as a conventional balloon dilatation catheter for angioplasty procedures. Balloon 14 may be formed of suitable materials such as polyethylene, polyvinyl chloride, polyethylene terephthalate and other like polymers. In order for stent 10 to remain in place on balloon 14 during delivery to the site of the damage within artery 15, stent 10 is compressed onto balloon 14.

An optional retractable protective delivery and alignment sleeve 20 may be provided to further ensure that stent 10 stays in place on balloon 14 of delivery catheter 11 and to prevent abrasion of the body lumen by the open surface of stent 10 during delivery to the desired arterial location. A removable tubular shape carrier (not shown) might be used in place of or in addition to sleeve 20 for the same purposes. Other means for securing stent 10 onto balloon 14 may also be used, such as providing collars or ridges on the ends of the working portion, i.e., the cylindrical portion of balloon 14.

In order to implant stent 10, it is first mounted onto inflation balloon 14 on the distal extremity of delivery catheter 11. Stent 10 is crimped down onto balloon 14 to ensure a low profile. The present invention addresses this crimping procedure.

The catheter-stent assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the catheter-stent assembly is advanced over guide wire 18 within artery 15 until stent 10 is directly under detached lining 16. Prior to inflation of balloon 14, delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

Figure 2:
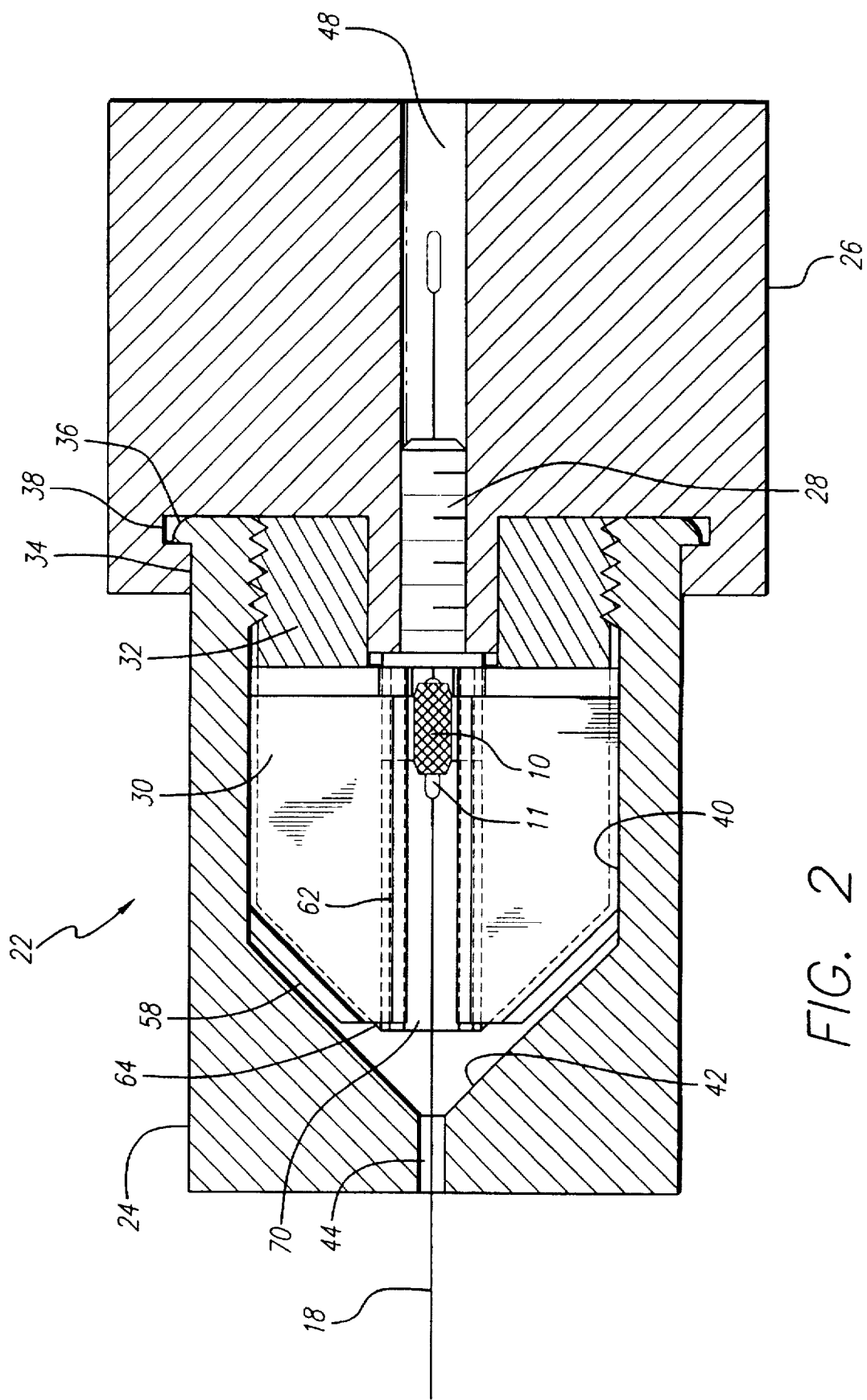
FIG. 2 is a cross-sectional view of a preferred embodiment of the present invention stent crimping tool exposing the internal assembly of components.

FIG. 2 is a sectional view of a preferred embodiment of the present invention stent crimping tool 22. As recognized in this sectional view, the present invention stent crimping tool 22 is characterized by a preferably cylindrical housing made of two interlocking parts. Those parts are, namely, proximal section 24 and distal section 26 of the housing. The two parts are preferably interconnected by inserting a portion of proximal section 24 into corresponding space 34 formed into distal section 26, and engagement of lip 36 within groove 38 of distal section 26. With this type of interconnection, relative rotation between proximal section 24 and distal section 26 is possible while relative linear displacement is limited insofar as lip 36 is locked within groove 38.

Figure 3:
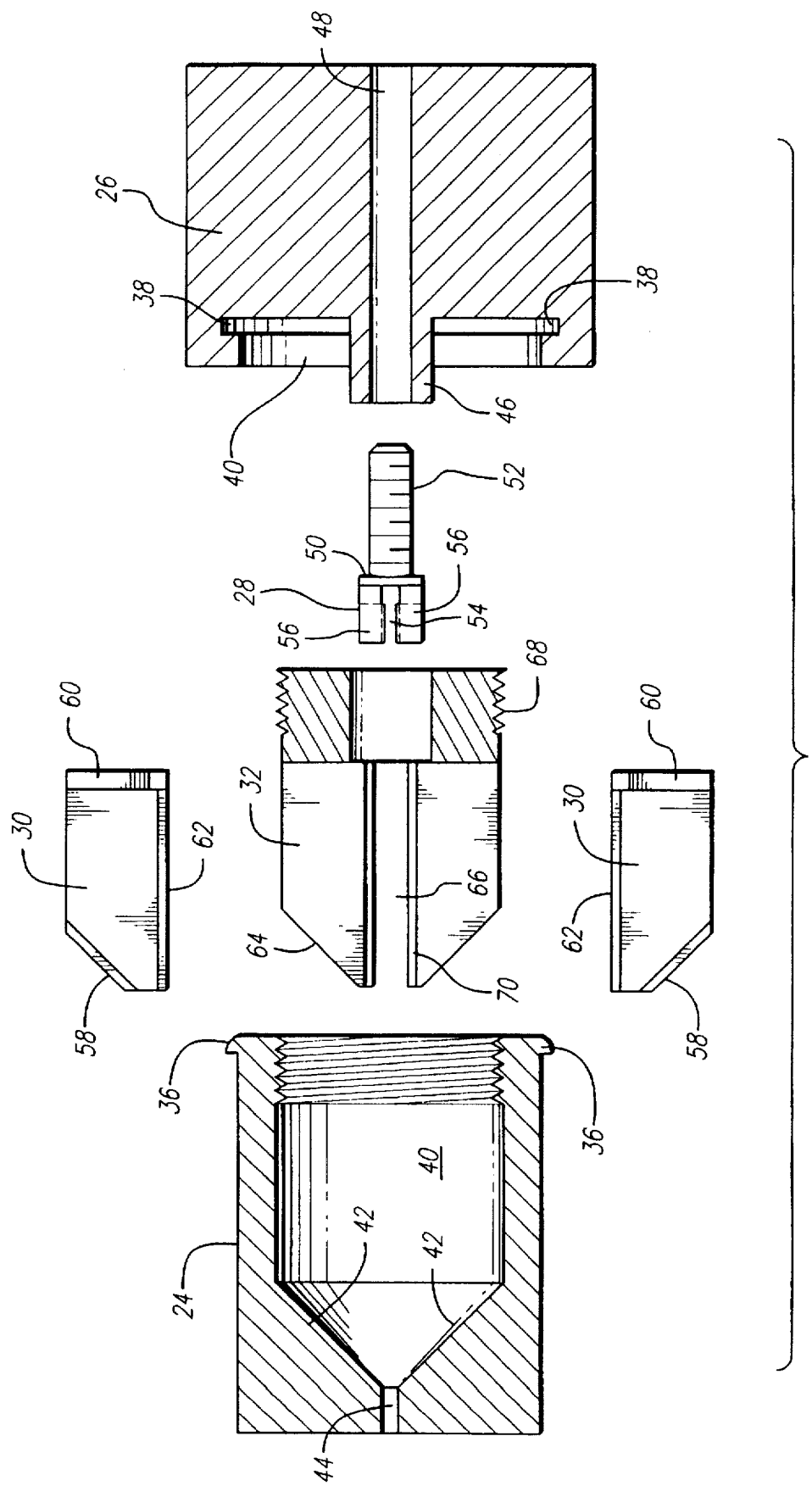
FIG. 3 is a side elevational, exploded view of the crimping tool shown in FIG. 2.

FIG. 2 thus provides a cross-sectional view of a preferred embodiment of the present invention in its assembled form. FIG. 3, on the other hand, is an exploded side elevational view of the major components of the present invention. In particular, FIG. 3 as well as FIG. 2 show the present invention being comprised of, moving from one end to the opposite end: proximal section 24, teeth 30, collar 32 screw feed 28 and distal section 26. In FIG. 3, intravascular stent 10, delivery catheter 11, and guide wire 18 have been omitted for clarity.

FIGS. 4A and 4B provide a sectional and a rear elevational view, respectively, of proximal section 24. As seen in the drawings, proximal section 24 is preferably cylindrical in shape having cylindrical cavity 40, wherein cylindrical cavity 40 includes tapered end 42 leading to opening 44. In the preferred embodiment, tapered end 42 has a 45 degree taper from a central axis of proximal section 24. Also seen in FIGS. 4A and 4B is lip 36 which, as seen in FIG. 2, helps secure proximal section 24 to distal section 26. To facilitate assembly with collar 32, proximal section 24 has a five degree coarse thread 72 cut into the wall of cylindrical cavity 40.

FIGS. 6A and 6B provide a side elevational and an end view, respectively, of distal section housing 26. In the preferred embodiment shown here, distal section 26 has an ergonomic cylindrical shape with cylindrical cavity 40 and groove 38 used to catch lip 36. Distal section 26 also includes boss 46 with tubular passage 48 extending therethrough. The end portion of tubular passage 48 extending through boss 46 is tapped to a ¼"-20 threads to accept a threaded screw.

FIGS. 8A and 8B provide a front elevational and a side elevational view, respectively, of screw feed 28. As a device that translates rotational motion to linear motion, screw feed 28 is comprised of head 50 and shaft 52, the latter being cut with ¼"-20 threads to match the corresponding threads formed in boss 46 of distal section 26.

Screw feed 28 further includes hollow core 54 that extends a length of head 50 and shaft 52. Hollow core 54 serves as a chamber to hold stent 10. In addition, screw feed 28 includes preferably four orthogonal slots 56. These slots 56 are designed to receive and retain teeth 30.

FIGS. 7A, 7B, and 7C provide a top plan, a front elevational, and a side elevational view, respectively, of a preferred embodiment tooth 30. Tooth 30 is essentially a flat, almost trapezoidal shape plate having angular proximal edge 58 formed at preferably 45 degrees in one corner of the plate.

Along angular proximal edge 58 and along distal edge 60 are "T" formations. The "T" formation along distal edge 60 of tooth 30 conforms and slides into complementary "T" cuts in slots 56 of screw feed 28. A "T" formation is best seen in distal edge 60 of FIG. 7A, and a corresponding "T" cut is best seen formed in head 50 of FIG. 8B. The "T" formation along angular proximal edge 58 conforms and slides into a complementary "T" cut formed in orthogonal slot 66 of collar 32. As seen in FIG. 2, one function of the "T" formations is to slidably retain teeth 30 in their respective slots 56 when teeth 30 are assembled to screw feed 28.

Radiused edge 62 extends into hollow core 54 of screw feed 28. As best seen in FIG. 7B, at the crest of radiused edge 62 is a groove having radius 74 that defines the final outside diameter of stent 10 after undergoing the crimping procedure. In a preferred embodiment, this radius 74 is in the order of 0.007 inch. Needless to say, changing the size or shape of radius 74 changes the final outside diameter of the crimped stent.

In an alternative embodiment (not shown), the radiused edge may have a contour. The contour from a cross-sectional point of view, either axially or radially, may have a rectangular, arcuate, diamond, saw tooth, sinusoidal, ridged, or like profile known in the art. Such radiused edges help improve stent retention.

FIGS. 5A and 5B provide a front elevational and a side elevational view of a preferred embodiment of collar 32. As best seen in those drawings, collar 32 has a generally cylindrical shape with a conical end 64 angled at approximately 45 degrees from a horizontal axis. Accordingly, conical end 64 and the cylindrical body of collar 32 are adapted to fit within tapered end 42 and cylindrical cavity 40.

As mentioned earlier, four orthogonal slots 66 are formed into collar 32 through which four teeth 30 pass. Angular proximal edge 58 of each tooth 30 is retained in collar 32 by "T" formations formed along angular proximal edge 58 sliding inside "T" cuts formed in orthogonal slots 66.

At a distal end of collar 32 are five degree coarse threads 68 intended to match threads 72 in proximal housing 24. Threads 68 and 72 retain collar 32 immovably inside cylindrical cavity 40 of proximal housing 24. Collar 32 further includes tubular passage 70 in communication with opening 44. Passage 70 extends the entire length of collar 32.

All together, the foregoing structures are assembled according to that shown in FIGS. 2 and 3. More precisely, teeth 30 are slid into corresponding slots 66 of collar 32 and extend into slots 56 formed in head 50 of screw feed 28. Thus joined, screw feed 28 cannot rotate because it is linked via teeth 30 to collar 32, which is tightly screwed into proximal section 24.

Head 50 of screw feed 28 extends into passage 70 within collar 32 while threaded shaft 52 is screwed into boss 46 of distal section housing 26. Uncrimped intravascular stent 10 is placed in hollow core 54. The major pieces of the housing are assembled as shown in FIG. 2 so that lip 36 latches or snaps into groove 38 while collar 32 is immovably mounted to cylindrical cavity 40 of proximal section housing 24.

The next step is to load stent 10 onto delivery catheter 11. This is accomplished by inserting guide wire 18 into opening 44 of proximal section 24 and through passage 70 of collar 32, extending out hollow core 54. The present invention tool 22 can then be advanced along guide wire 18. Balloon catheter 11 and a mandrel (not shown) are advanced over guide wire 18 into passage 70. In an alternative embodiment, the mandrel may be built into the present invention tool so that it extends therefrom, and the catheter is guided onto the mandrel and into the correct position every time.

The user then manually aligns balloon 14 with uncrimped stent 10 inside hollow core 54. Alignment is possible when key structures of tool 22 are formed from a transparent or translucent material so that the user can see the location of the two parts. Other alignment methods known in the art can be employed as well.

Next is the crimping step. The user holds proximal section 24 while twisting distal section 26. Because their relative linear motion is held constant, the relative rotational movement of proximal section 24 and distal section 26 causes screw feed 28 to advance out of boss 46. As described above, screw feed 28 does not rotate relative to proximal section housing 24 due to the presence of teeth 30 extending between head 50 and immobilized collar 32.

As screw feed 28 advances toward proximal section 24, it carries forward teeth 30 so that angular proximal edges 58 of each tooth 30 encounters tapered end 42, which in turn forces teeth 30 to converge radially inward. As this convergence occurs, radius edges 62 of teeth 30 engage and crimp the underlying stent 10 onto balloon catheter 11. Teeth 30 thus act as jaws closing down on stent 10. The mandrel optionally loaded into delivery catheter 11 prevents the crimping process from overly compressing stent 10 onto catheter 11.

Rotating distal section 26 in the opposite direction moves screw feed 28 in a direction away from tapered end 42 of proximal section 24. As a result, pressure from radiused edges 62 of teeth 30 is removed from crimped stent 10. Thereafter, the user may freely push the crimped stent and catheter assembly through passage 70 so that the combination appears outside the present invention tool 22 for implantation in a patient. Of course the foregoing steps for crimping the stent can be repeated as necessary.

Optional markings (not shown) on an exterior surface of proximal section 24 or distal section 26 may help the user determine the amount of twisting needed to achieve a particular crimp. The markings can be calibrated at the factory for a given size of stent.

The shape of the present invention tool may be changed to offer improved ergonomics for the user. It is expected that the present invention tool is machined from acrylic or lexan. Later versions of the present invention tool may be created from alternative materials that offer comparable shielding from a radioactive stent.

Moreover, radiused edges 62 of teeth 30 may be coated or covered with a protective material. Radiused edge 62 may be polished as well so that they do little harm to the polished finished of stent 10. In alternative embodiments, there may be more or fewer than four teeth as described above. Naturally, the number of slots in the collar and screw feed and their angular placement surrounding the stent should be modified as necessary, and the arc defining the radiused edge of each tooth should be modified too.

The present invention is sterilized and intended to be used in a cath lab by a trained technician or cardiologist. More precisely, as will be appreciated by those skilled in the art, the present invention crimping tool 22 is designed both for single use applications in a cath lab by a physician, or for multiple use applications in a sterile environment in a high volume manufacturing facility. In such a manufacturing facility where sterile conditions exist, stent crimping tool 22 can be used repeatedly to crimp stents onto balloons until the mechanism wears out. Thus, repeated uses of the present invention are contemplated for controlled, sterile environments, as are single use applications when operated by cath lab personnel.

Furthermore, the present invention crimping tool can be used with any stent that is released without a delivery system. The crimping tool may also be sold alone, because its design is robust enough to undergo many uses.

Other modifications can be made to the present invention without departing from the scope thereof The specific dimensions, procedural steps, and materials of construction are provided as examples, and substitutes are readily contemplated which do not depart from the invention.

What is claimed is:

1. A tool for crimping a stent onto a balloon catheter, comprising:
   a housing including a proximal section and a distal section, wherein the proximal section includes a cylindrical cavity having a tapered end and an opening in communication with the cavity;
   a cylindrical collar having a conical end conforming to the tapered end of the cylindrical cavity when positioned therein, wherein the collar includes a plurality of slots extending radially and along a length thereof and intersecting at the conical end, and having a passage therethrough in communication with the opening in the proximal section;
   a plurality of plates, each plate having an angular proximal edge, and being slidably disposed inside a corresponding slot in the collar, each plate having a radiused edge extending into the passage; and
   a screw feed extending into the passage wherein the screw feed includes radial slots that lead into a hollow core, and the slots receive the respective radiused edges of the plates extending therein, and wherein the screw is threaded to the distal section of the housing;
   whereby an uncrimped stent loaded on the balloon catheter is located in the hollow core, whereby rotating the distal section of the housing advances the screw and the angular proximal edge of the plates into the tapered end thereby displacing the plates radially inward so that the radiused edges of the plates crimp the stent onto the balloon catheter.

2. The crimping tool of claim 1, wherein the radiused edge includes a radius that approximates an outside diameter of a crimped stent.

3. The crimping tool of claim 1, wherein the tool includes translucent polymer.

4. The crimping tool of claim 1, wherein the tool includes a polymer selected from the group consisting of acrylic or lexan.

5. The crimping tool of claim 1, wherein the tool includes a mandrel disposed within the balloon catheter.

6. The crimping tool of claim 1, wherein the collar includes four slots disposed radially at right angles.

7. The crimping tool of claim 1, wherein the collar is affixed to the housing.

8. The crimping tool of claim 1, wherein the distal section of the housing includes a groove to receive a lip formed in the proximal section of the housing to facilitate relative rotational motion only.

9. The crimping tool of claim 1, wherein the housing includes reference markings on an exterior surface.

10. The crimping tool of claim 1, wherein the radiused edge of each plate is contoured.

11. A tool for crimping a stent onto a balloon catheter, comprising:
   a housing including a proximal section rotatably attached to a distal section, wherein the proximal section includes a cylindrical cavity having a tapered end, and an opening in communication with the cavity;
   a cylindrical collar affixed to the proximal section of the housing having a conical end approximating the tapered end, wherein the collar includes a plurality of slots extending radially and along a length thereof and intersecting at the conical end, and having a cylindrical passage therethrough in communication with the opening in the housing;
   a plurality of plates, each plate having an angular proximal edge approximating the tapered end, and being slidably disposed inside a corresponding slot in the collar, each plate having a radiused edge extending into the cylindrical passage; and
   a screw feed extending into the cylindrical passage and is threaded to the distal section of the housing, and wherein the screw feed includes a head with a hollow core that is in communication with the cylindrical passage, and the head further includes radial slots aligned with the slots in the collar such that the radiused edges of the plates extend through the slots into the hollow core;
   whereby an uncrimped stent loaded on the balloon catheter is positioned in the hollow core, whereby rotating the distal section of the housing advances the screw feed and the angular proximal edge of the plates into the tapered end thereby displacing the plates radially inward so that the radiused edges of the plates crimp the stent onto the balloon catheter.

12. The stent crimping tool of claim 11, wherein the housing includes a cylindrical exterior.

13. The stent crimping tool of claim 11, wherein the radiused edges of the plates are coated with a material selected from the group consisting of Teflon, a lubricious polymer, or a biocompatible coating.

14. The stent crimping tool of claim 11, wherein the tool includes a material that absorbs radiation.

15. A method of crimping a stent onto a balloon catheter comprising the steps of:

providing a housing including a proximal section rotatably mounted to a distal section, wherein the proximal section includes a cylindrical cavity having a tapered end with an opening;

providing a cylindrical collar having a conical end, wherein the collar includes a plurality of slots extending radially and along a length thereof and intersecting at the conical end, and having a cylindrical passage therethrough in communication with the opening;

mounting the cylindrical collar to the proximal section so that the conical end conforms with the tapered end;

providing a plurality of plates, each plate having an angular proximal edge, and being slidably disposed inside a corresponding slot in the collar, each plate having a radiused edge extending into the passage;

providing a screw feed extending into the cylindrical passage and threaded to the distal section of the housing, and wherein the screw feed includes a head with a hollow core that is in communication with the cylindrical passage, and the head further includes radial slots aligned with the slots in the collar such that the radiused edges of the plates extend through the slots into the hollow core;

placing an uncrimped stent in the hollow core of the screw feed;

advancing a balloon catheter through the passage into the hollow core;

loading the stent onto the balloon catheter; and rotating the distal section of the housing to advance the screw feed and the angular proximal edge of the plates into the tapered end thereby displacing the plates radially inward so that the radiused edges of the plates crimp the stent onto the balloon catheter.

16. The method of claim 15, wherein the collar, plates, and housing include a transparent polymer so that the crimping step is visible.

17. The method of claim 15, wherein the method further comprises the step of advancing a guide wire through the opening, the cylindrical passage, and the hollow core holding the stent.

18. The method of claim 15, wherein the method further comprises the step of inserting a mandrel inside the balloon catheter.

19. The method of claim 15, wherein the method further comprises the step of providing a distal section of the housing having a cylindrical exterior.

20. The method of claim 15, wherein the method further comprises the steps of providing a marking on an exterior of the proximal section and distal section of the housing, and rotating the distal section until the markings are aligned.

21. The method of claim 15, wherein the method further comprises the step of providing a mandrel in the hollow core, and centering the hollow core holding the stent on the mandrel.

22. The method of claim 15, wherein the radiused edge of each plate has a contour.

* * * * *